United States Patent [19]

Denis et al.

[11] Patent Number: 5,286,629
[45] Date of Patent: Feb. 15, 1994

[54] METHOD OF BINDING A PRODUCT TO THE MEMBRANE OF A KERATINOCYTE BY MEANS OF A LIGAND-RECEPTOR BOND, METHOD OF PREPARING SUCH A PRODUCT, PRODUCT OBTAINED, COSMETIC OR PHARMACEUTICAL COMPOSITION IN WHICH IT IS PRESENT AND ITS METHOD OF PREPARATION

[75] Inventors: Alain Denis, Loges; Claudine Kieda, Orleans; Michel Monsigny, Saint Cyr En Val; Pierre Perrier, Orleans; Gérard Redziniak, Saint Cyr En Val, all of France

[73] Assignee: Parfums Christian Dior, Paris, France

[21] Appl. No.: 761,809

[22] PCT Filed: Mar. 16, 1990

[86] PCT No.: PCT/FR90/00176

§ 371 Date: Nov. 4, 1991

§ 102(e) Date: Nov. 4, 1991

[87] PCT Pub. No.: WO90/11069

PCT Pub. Date: Oct. 4, 1990

[30] Foreign Application Priority Data

Mar. 20, 1989 [FR] France .................. 89 03628

[51] Int. Cl.$^5$ .................. A61K 9/127; A61K 47/48
[52] U.S. Cl. .................. 435/7.1; 436/503; 424/70; 424/450; 514/844; 435/7.2
[58] Field of Search .................. 424/450, 70, 574; 514/844; 435/7.1, 7.2; 436/503

[56] References Cited

U.S. PATENT DOCUMENTS

| 3,969,540 | 7/1976 | Jensen ........................ 426/657 |
| 4,508,693 | 10/1990 | Siddiqi et al. ............ 435/7.7 |
| 4,826,680 | 5/1989 | Jaeger ........................ 435/69 |

FOREIGN PATENT DOCUMENTS

| 028917 | 5/1981 | European Pat. Off. . |
| 0285178 | 10/1988 | European Pat. Off. . |
| 2609397 | 7/1988 | France . |
| WO86/05789 | 10/1986 | World Int. Prop. O. . |
| WO87/05300 | 9/1987 | World Int. Prop. O. . |

OTHER PUBLICATIONS

Chemical Abstracts, vol. 106, No. 23, 106:193579j, Jun. 8, 1987.
Biochimica et Biophysica Acta, vol. 946, 1988, Elsevier Science Publishers B.V., J. Haensler et al.: "Preparation of neo-galactosylated liposomes and their interaction with mouse peritoneal macrophages", pp. 95–105, see especially p. 99, FIG. 1.

Primary Examiner—Ronald W. Griffin
Attorney, Agent, or Firm—Rosen, Dainow & Jacobs

[57] ABSTRACT

The invention relates to products which are to be bound specifically to the membrane of a keratinocyte by means of a ligand-receptor bond.

These products carry at least one ligand consisting of an oside residue selected from α-L-rhamnose, α-D-galactose and α-D-galactose-6-phosphate.

By virtue of this specificity, it is possible to prepare cosmetic or pharmaceutical compositions having an improved efficacy in particular, for example for regeneration of the epidermis, for the treatment of psoriasis or for renewed hair growth.

59 Claims, 3 Drawing Sheets

METHOD OF BINDING A PRODUCT TO THE MEMBRANE OF A KERATINOCYTE BY MEANS OF A LIGAND-RECEPTOR BOND, METHOD OF PREPARING SUCH A PRODUCT, PRODUCT OBTAINED, COSMETIC OR PHARMACEUTICAL COMPOSITION IN WHICH IT IS PRESENT AND ITS METHOD OF PREPARATION

The present invention relates essentially to a method of binding a product to the membrane of a keratinocyte by means of a ligand-receptor bond, to a method of preparing such a product, to the product obtained, to a cosmetic or pharmaceutical composition in which it is present and to its method of preparation.

The existence of processes for the recognition of cells, for example in relation to other cells or substances such as proteins, has been known for a long time. These processes act by way of a reaction between a ligand and a receptor present on the surface of the cells.

For example, the recognition of surface antigens by monoclonal antibodies is known, this phenomenon being utilized in therapeutic or diagnostic applications. There may be cited, for example, French patent document A1-2 606 034, which describes antibodies capable of recognizing a new surface protein and of being used especially as reagents in techniques based on the antigen-antibody reaction.

Recognition processes are also known which involve sugars. These are recognized specifically by membrane receptors. However, the sugars recognized are not the same from one type of cell to another. It is known, for example, that rat hepatocytes specifically recognize galactose (Ashwell G. and Morell A. G., Advan. Enzymol. (1974) 41, 99–128) whereas human fibroblasts recognize mannose-6-phosphate.

Based on this acquired knowledge, attempts have been made to develop targeted drug delivery systems making it possible to reach those sites in the organism on which it is desired to act. Liposomes have been used in particular for this purpose.

Since their discovery by BANGHAM (J. Mol. Biol., 13, 238–252 (1965)), liposomes have been used as vehicles for medicinal or other active principles (see, for example, French patent documents A-2 221 122, A-2 415 460 or A-2 540 381).

French patent document A-2 609 397 relates to the use of a substance or composition of carbohydrate type as the active principle of a dermatological, cosmetological, pharmaceutical or cell stimulating composition for the purpose of boosting the cell or tissue bioenergetic potential (see claim 1) or for improving skin comfort, by virtue of their moisturizing, smoothing and softening effect (page 3, line 33 to page 4, line 10, where even an antiinflammatory action is indicated).

Said document therefore concerns a general teaching which does not relate to the particular problem of keratinocytes.

Patent document PCT/WO 87/05300 to BIOCOMPATIBLES LTD relates to a method of preserving a material having a water-dependent structure, which comprises bringing the material into contact with an aqueous solution of a polyhydroxyl compound and then removing the water from this material, the object being to permit the long-term preservation of biological materials such as hemoglobin, erythrocytes, liposomes and cells (see page 1, lines 1 to 4).

Said document concerns the problem of the drying of proteins from aqueous solutions containing saccharides in order to avoid chemical and physical degradation processes (see page 3, 2nd complete paragraph).

More recently, it has been proposed to give liposomes specificity (see BARBET J. et al., "Monoclonal Antibody covalently coupled to liposomes: Specific Targeting to Cells" in J. Supramol. Struct. Cell. Biochem., 16, 243–258 (1981, and LESERMAN L. D. et al., "Targeting to Cells of fluorescent Liposomes covalently coupled with Monoclonal Antibodies or protein A" in Nature, 228, 602–604 (1980)).

Furthermore, patent document WO 88/00474 describes a lipid membrane structure comprising a lipid vesicle encapsulating a drug, and a ligand containing a residue specific for hepatobiliary receptors, for the purpose of directing the structure towards the hepatocytes with an exceptional efficacy.

European patent document A-0 028 917 relates to lipid vesicles carrying hydrocarbon surfaces as lymphatically targeted vehicles for therapeutic and diagnostic purposes. Said document does not concern the targeting of keratinocytes.

European patent document A-0 285 178 relates to mannobiose derivatives which are useful as a component for modifying pharmaceutical preparations, such as liposomes, having a specific affinity for the Kupffer cells of the liver.

The abstract of STN database of KARLSRUHE, vol. 106, of Jun. 8, 1987, abstract 193579j, cites an article by TODA, in Journal of Investment Dermatology, 88(4), 412–417, which deals with the culture of freshly isolated human keratinocytes on substrates bound to a different ligand, including fibronectin, collagen or a structure membrane.

Said document goes in a totally different direction from that forming the subject of the invention.

In fact, said document recommends a specific culture of the keratinocytes in order to activate them with a view to activating their capacity to multiply on all substrates coated with ligands.

This article demonstrates that the invention described below was not at all evident to those skilled in the art.

Finally, patent application PCT/WO 86/05789 to BIOCARB also relates to hydrocarbon derivatives in the context of specific targeting for a therapeutic or diagnostic purpose, this targeting being effected on molecules of different organs of mammals, including man (see page 1, lines 4 to 8).

It is apparent from the objects indicated on page 2 that the invention described in said document relates to the detection of pathogenic bacteria by particular receptors.

This therefore has nothing at all to do with the problem of the targeting of keratinocytes, which is the subject of the invention described below.

As far as the skin is concerned, it is seen that there is an obvious advantage in dermatological and especially cosmetic products, applied locally, binding preferentially and specifically in the epidermis. Binding to the membrane receptors of the keratinocytes, which are the essential cells of the epidermis, constitutes a solution to this problem.

Now, no sugar receptors on the surface of keratinocytes were known hitherto.

According to the present invention, it has been discovered, totally unexpectedly, that a product can be bound to the membrane of a keratinocyte by means of a ligand-receptor bond when using a product carrying at least one ligand consisting of an oside residue selected from rhamnose, galactose and galactose-6-phosphate. It has in fact been discovered, unexpectedly, that rhamnose, galactose and galactose-6-phosphate are specific ligands for the receptor sites of the membrane of keratinocytes. It has also been observed that α-L-rhamnose and α-D-galactose-6-phosphate have a considerably greater specificity than α-D-galactose and are thus preferred to the latter.

Moreover, it has also been demonstrated that the product carrying this sugar forming a specific ligand for the receptors of the membrane of keratinocytes can take a variety of forms. For example, it can be a submicroscopic particle such as a liposome or a polymeric nanoparticle, or a molecule or macromolecule of natural or synthetic origin, such as a protein. Also, the sugar forming the ligand can be coupled in various ways to the surface of this product. It can advantageously be coupled by a covalent chemical bond, preferably via a spacer arm.

Thus the object of the present invention is to solve the new technical problem which consists in providing a solution making it possible specifically to bind a product to the membrane of keratinocytes by means of a ligand-receptor bond, if appropriate at the expense of other categories of cells surrounding the keratinocytes.

The object of the present invention is to solve the above new technical problem by means of an extremely simple, rapid, practical and reliable method. A further object of the present invention is to solve this new technical problem by providing a method of selecting a product capable of binding specifically to the membrane of a keratinocyte by means of a ligand-receptor bond, said method being particularly simple, rapid, practical and reliable.

A further object of the present invention is to solve the afore-mentioned new technical problem by providing a method of preparing such a product capable of binding specifically to the membrane of a keratinocyte by means of a ligand-receptor bond, said method also being simple, rapid, practical and reliable. A further object of the present invention is to solve the afore-mentioned new technical problem by providing a product capable of binding specifically to the membrane of a keratinocyte by means of a ligand-receptor bond, said product being in a form which is particularly easy to handle, being reliable and being able to be used rapidly without requiring particular steps. A further object of the present invention is to solve the afore-mentioned new technical problem by providing a cosmetic or pharmaceutical composition, especially a dermatological composition, and its method of preparation, incorporating such a specific product, which has all the afore-mentioned decisive technical advantages relating to the reliability of the specific binding to the membrane of a keratinocyte by means of a ligand-receptor bond using a rapid and practical method.

The present invention solves the afore-mentioned technical problem by providing the afore-mentioned solutions in an extremely simple manner which can be used on the industrial scale.

Thus, according to a first feature, the present invention provides a method of binding a product to the membrane of a keratinocyte by means of a ligand-receptor bond, which comprises using a product consisting of a basic structure coupled to at least one ligand consisting of an oside residue accessible to the membrane receptors, said oside residue being selected from rhamnose, galactose and galactose-6-phosphate and preferably from α-L-rhamnose and α-D-galactose-6-phosphate. It should be noted that the invention includes all the isomeric forms of rhamnose and galactose.

According to one advantageous characteristic, the ligand is coupled to the surface of said basic structure by a covalent chemical bond.

According to another advantageous characteristic of the method according to the invention, the ligand is coupled to the surface of the afore-mentioned basic structure via a spacer arm such as the residue of a heterobifunctional reagent or a group of several sugars like the (1-4)-O-β-D-glucopyranosyl-(1-6)-O-β-D-glucopyranosyl group. Such spacer arms are well known to those skilled in the art, who will be able to refer for example to the article by J. S. Slama and R. R. Rando in Biochemistry, 1980, 19, 4595–4600.

According to another particularly advantageous characteristic of the method according to the invention, the afore-mentioned product is a submicroscopic particle such as a liposome or a polymeric nanoparticle.

According to yet another particularly advantageous characteristic of the method according to the invention, the afore-mentioned product is a molecule or macromolecule of natural or synthetic origin, such as an asiaticoside containing α-L-rhamnose, extracted in particular from the plant *Centella asiatica*, available for example from Inverni Della Beffa, a digalactosyldiglyceride obtained especially from a wheat flour extract, available for example from Sigma, or a neoglycoprotein obtained for example by combining a serum albumin (SA), for example bovine or human serum albumin, with one of the afore-mentioned sugars.

According to another characteristic of the method according to the invention, the afore-mentioned product is or contains a substance of cosmetic or pharmaceutical interest, especially dermatological interest, such as an agent for modulating the metabolism of the skin cells.

According to a second feature, the present invention also provides a method of selecting a product which is to be bound to the membrane of a keratinocyte by means of a ligand-receptor bond, which comprises selecting, from a group of products, those consisting of a basic structure coupled to at least one ligand consisting of an oside residue accessible to the receptors, said oside residue being selected from rhamnose, galactose and galactose-6-phosphate, preferably α-L-rhamnose and α-D-galactose-6-phosphate.

According to a third feature, the present invention also provides a method of preparing a product which is to be bound to the membrane of a keratinocyte by means of a ligand-receptor bond, which comprises coupling a corresponding basic structure to at least one ligand consisting of an oside residue accessible to the membrane receptors, said oside residue being selected from rhamnose, galactose and galactose-6-phosphate, preferably α-L-rhamnose and α-D-galactose-6-phosphate.

According to one particularly advantageous characteristic, the afore-mentioned ligand is coupled to the basic structure by a covalent chemical bond. The coupling can be effected in accordance with the general method described by Mac Broom in Methods in Enzymology (1972) 28, 212–222, or else the method described by F. J. Martin and D. Papahadjopoulos in The Journal of Biological Chemistry (1982), vol. 257, no 1, pages 286–288.

According to another advantageous characteristic of the method according to the invention, the afore-mentioned ligand is coupled to the basic structure via a spacer arm such as defined above.

According to yet another advantageous characteristic of the method according to the invention, the basic structure is a submicroscopic particle such as a liposome or a polymeric nanoparticle.

According to yet another characteristic of the method according to the invention, the afore-mentioned basic structure is a molecule or macromolecule of natural or synthetic origin, such as a protein, for example a serum albumin.

According to yet another advantageous characteristic of the method according to the invention the afore-mentioned product is or contains a substance of cosmetic or pharmaceutical interest, especially dermatological interest, such as an agent for modulating the metabolism of the skin cells.

According to a fourth feature, the invention also covers a product which is to be bound to the membrane of a keratinocyte by means of a ligand-receptor bond, said product being obtained by one of the methods defined above. The invention also covers the novel products capable of binding to the membrane of a keratinocyte by means of a ligand-receptor bond, said products comprising at least one ligand consisting of an oside residue accessible to the membrane receptors, said oside residue being selected from rhamnose, galactose and galactose-6-phosphate and preferably α-L-rhamnose and α-D-galactose-6-phosphate, and coupled to a basic structure selected for example from the group consisting of a submicroscopic particle such as a liposome or a polymeric nanoparticle, a molecule or macromolecule of natural or synthetic origin, such as a protein, in particular a serum albumin, and a substance of cosmetic or pharmaceutical interest, especially dermatological interest, such as an agent for modulating the metabolism of the skin cells. According to an advantageous characteristic, this coupling takes place via a spacer arm such as the residue of a heterobifunctional reagent or a group of several sugars like the (1-4)-O-β-D-glucopyranosyl-(1-6)-O-β-D-glucopyranosyl group.

According to a fifth feature, the present invention also provides a cosmetic or pharmaceutical composition, especially a dermatological composition, which contains at least one product such as obtained by the method described above or such as defined above.

According to an advantageous characteristic of the invention, the afore-mentioned composition is intended for any care or any treatment affecting the keratinocytes, for example the improvement of skin regeneration, the treatment of psoriasis or renewed hair growth.

Finally, the invention further relates to a method of preparing a cosmetic or pharmaceutical composition, especially a dermatological composition, wherein at least one product such as obtained by one of the methods described above, or such as defined above, is associated with a cosmetically or pharmaceutically acceptable excipient, vehicle or carrier. Likewise, the invention also covers a method of care or treatment affecting the keratinocytes, for example with a view to skin regeneration, the treatment of psoriasis or renewed hair growth, which comprises applying the product such as obtained above by one of the methods described above, or such as defined above, in a cosmetically or therapeutically effective amount, advantageously when said product is associated with a cosmetically or pharmaceutically acceptable vehicle, carrier or excipient.

It can be seen that the invention makes it possible to achieve the cell targeting of a product, which can thus be concentrated specifically at the keratinocytes by virtue of the presence of at least one specific ligand consisting of an oside residue selected from rhamnose, galactose and galactose-6-phosphate, preferably α-L-rhamnose and α-D-galactose-6-phosphate.

Within the framework of the present invention, the product to which the specific ligand consisting of the oside residue is coupled is of an arbitrary nature.

It is possible, for example, to use a protein to which one of the afore-mentioned sugars is coupled by a synthetic method.

In an advantageous embodiment of the invention, the number of oside residues, such as defined above, carried by the protein is at least about twenty.

Another basic product which can be used is a submicroscopic particle such as a lipid vesicle, which can be in the form of a liposome.

Within the framework of the present invention, the adjective "lipid" covers all substances comprising a so-called fatty carbon chain generally longer than 5 carbon atoms, this substance normally being called a "lipid".

According to the invention, amphiphilic lipids, i.e. lipids consisting of molecules possessing either an ionic or a non-ionic hydrophilic group and a lipophilic group, are used as the lipid for forming the afore-mentioned liposome, these amphiphilic lipids being capable of forming lipid lamellar phases or liposomes in the presence of an aqueous phase.

The following may be mentioned in particular among these lipids: phospholipids, phosphoaminolipids, glycolipids, polyethoxylated fatty alcohols and polyethoxylated or non-polyethoxylated polyol esters. Such substances consist for example of an egg or soya lecithin, a phosphatidylserine, a sphyngomyelin, a cerebroside or an ethoxylated polyglycerol stearate.

According to an advantageous characteristic of the present invention, as far as liposomes are concerned, the proportion of glycoside derivatives according to the invention, as a molar percentage of all the lipid molecules forming the bilayer of the liposome, is at least 10% and preferably at least 15% relative to all the amphiphilic lipids of the liposome.

It is also preferable, according to the invention, for the liposomes to be formulated so as to have a high microviscosity. This can be achieved for example by using amphiphilic lipids whose transition temperature is above about 37° C. and preferably 41° C., especially phospholipids or saturated fatty acids, for example dipalmitoylphosphatidylcholine.

It will also be noted that, because of the hydrophilicity of the oside residues, the latter distribute themselves on the outside of the lipid bilayer of the liposomes, some of them being orientated towards the inside and the others towards the outside of the liposome. It has moreover been observed that the smaller the liposomes are, the greater is the number of oside residues orientated towards the outside. Thus there is a sufficient number of them to be easily accessible to the keratinocyte receptors. It will be understood that this accessibility is even better if the oside residues are located at the end of a spacer arm.

According to the invention, another basic product which can be used is a polymeric nanoparticle with dimensions generally of less than a micrometer, preferably polymeric nanoparticles containing NH2 groups, alcohol groups or thiol groups permitting easy coupling with the oside residue according to the invention. It is preferable to choose biodegradable nanoparticles, such as polylactates, which are well known to those skilled in the art. Such particular particles containing NH2 groups are commercially available, for example from Interfacial Dynamics Corporation (Portland, Oreg. - USA).

According to an advantageous characteristic of the present invention, the oside residues coupled to the surface of said polymeric nanoparticles are selected from α-D-galactose, α-L-rhamnose and α-D-galactose-6-phosphate residues.

Porous nanoparticles can advantageously be used to encapsulate the active substances.

In an advantageous embodiment of the invention, the basic products, such as the afore-mentioned liposomes or nanoparticles, contain one or more substances of cosmetic or pharmaceutical interest, especially dermatological interest, such as an agent for modulating the metabolism of the skin cells, for example peptides obtained by the hydrolysis of proteins, and enzymic activity modulators, for example a xanthine such as theophylline.

The basic product which can be used according to the invention can also be the actual active substance of cosmetic or pharmaceutical interest, especially dermatological interest.

Other objects, characteristics and advantages of the invention will become clearly apparent from the following explanatory description with the aid of several Examples of the invention, which are given simply by way of illustration and cannot therefore in any way limit the scope of the invention. In the Examples, all the percentages are given by weight, unless indicated otherwise.

EXAMPLE 1 ACCORDING TO THE INVENTION

Preparation of Liposomes Carrying Rhamnosylated Residues

A. Coupling of α-L-rhamnose to a phospholipid

The coupling between a molecule of dipalmitoylphosphatidylethanolamine (DPPE) and a molecule of α-L-rhamnose (Rha) is effected by reacting p-phenylisothiocyanato-α-L-rhamnopyranoside (PPITC-α-L-rhamnopyranoside) with the amine group of DPPE.

The PPITC-α-L-rhamnopyranoside is prepared from p-aminophenyl-α-L-rhamnoside by reaction with thiophosgene in accordance with the method described by C. R. McBroom et al. in Methods in Enzymology (1972) 28, 212-222.

The commercial DPPE and the PPITC-α-L-rhamnopyranoside are dissolved in equimolar proportions, at 50° C., in a mixture consisting of a bicarbonate buffer (0.1 M, pH 9.5) and ethanol. The temperature is kept at 50° C. for 3 h, with stirring. The reaction medium is then cooled to about 4° C. and centrifuged.

The solid obtained after washing with distilled water is lyophilized to give a rhamnosylated DPPE (DPPE-Rha).

B. Preparation of the Liposomes

The following are weighed out:

| | |
|---|---|
| Dipalmitoylphosphatidylcholine (DPPC) | 48.6 mg |
| Cholesterol (chol) | 25.6 mg |
| Dicetyl phosphate (DCP) | 9.1 mg |
| Product according to the invention = DPPE-Rha | 16.7 mg |

After the afore-mentioned compounds have been mixed in a flat-bottomed flask, for example of 100 ml capacity, they are solubilized with a 7/1 chloroform-/methanol mixture in accordance with the rotary flask method described by Bangham in J. Mol. Biol., 13, 238-252 (1965). The solvents are then evaporated off at 55° C. under reduced pressure. The traces of solvents can be removed by means of a stream of nitrogen on the "greasy" film formed on the wall of the flask.

10 ml of the aqueous solution to be encapsulated are then added to the liposomes formed from the afore-mentioned lipid phase. This aqueous solution can for example contain a fluorescent marker consisting for example of the potassium salt of 5-(6)-carboxyfluorescein at a rate of 8 g per 40 ml of distilled water.

An equivalent amount of calcein blue can also be used as a fluorescent marker.

After 10 ml of the above aqueous solution to be encapsulated have been added, the mixture is stirred magnetically for 15 to 24 h in the dark.

The formation of large lipid vesicles is observed under the optical microscope.

The contents of the flask are transferred to a 30 ml vessel cooled in melting ice.

Preferably, the suspension is subjected to sonication for three times 2 min at 4° C. and at a power of 200 W, which makes it possible to form liposomes of substantially homogeneous size and of submicroscopic dimensions.

The liposome suspension obtained in this way can be kept at 4° C.

In a preferred embodiment, the liposomes are purified by being separated from the non-encapsulated aqueous phase by gel filtration, as is well known according to the conventional protocol for the purification of liposomes.

EXAMPLE 2 ACCORDING TO THE INVENTION

Preparation of Liposomes Carrying Rhamnosylated Residues Via Spacer Arms

A. Preparation of Rhamnose Carrying a Spacer Arm

An "activated sugar" of formula (I):

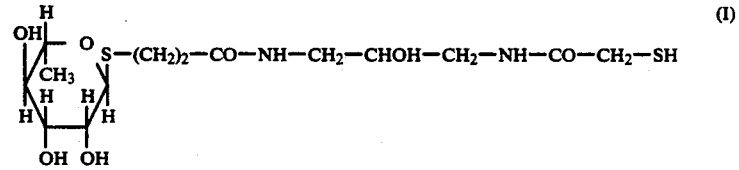

(I)

nopyranoside are dissolved in equimolar proportions, at 50° C., in a mixture consisting of a bicarbonate buffer (0.1 M, pH 9.5) and ethanol. The temperature is preconsisting of an α-L-rhamnopyranosyl residue in which the OH group located on the first carbon is substituted by a linear chain terminating in an SH group, is prepared as indicated below by carrying out the following successive steps:

Synthesis of 2,3,4-tri-O-acetyl-α-L-bromorhamnopyranoside (2)

The derivative (2) is obtained according to KEMPEN H. J. M. et al., J. Med. Chem. (1984) 27, 1306–1312, by reacting phosphorus bromide, $PBr_3$, (7 eq.) and water (50 eq.) with 1,2,3,4-tetra-O-acetyl-α-L-rhamnose (1) in acetic anhydride at 0° C., with stirring. The product (2) is recrystallized from a diisopropyl ether/hexane mixture.

Synthesis of 2-S-(2,3,4-tri-O-acetyl-α-L-rhamnopyranosyl)-2-thiopseudourea hydrobromide (3)

The derivative (3) is obtained according to CHIPOWSKY S. et al., Carbohyd. Res. (1973) 31, 339–346, by refluxing a mixture of equimolecular proportions of the derivative (2) and thiourea in anhydrous acetone under argon for 3 h. The product (3) is recrystallized from isopropanol.

Synthesis of 1-(2-carboxyethyl)thio-2,3,4-tri-O-acetyl-α-L-rhamnopyranoside (4)

The product (4) is obtained by reacting equimolecular proportions of the derivative (3) and 3-iodopropionic acid in solution in a 1:1 water/acetone mixture in the presence of 1.15 eq. of $Na_2CO_3$ and 2 eq. of $Na_2S_2O_5$. The reaction is followed by TLC (solvent: AcOEt/AcOH/$H_2O$ 8:2:1).

Synthesis of 1-(2-carboxyethyl)thio-α-L-rhamnopyranoside (5)

The derivative (5) is obtained by deacylating (4) in the presence of 4 eq. of triethylamine and 3 eq. of water in methanol. The reaction is followed by TLC (solvent: AcOEt/AcOH/$H_2O$ 8:2:1); it is complete after 6 days. The deacetylation product is isolated from the reaction medium by passage over a Dowex 1×2 column (HCOO-).

Synthesis of 1-(2-(3-amino-2-hydroxypropylaminocarbonyl)ethyl)thio-α-L-rhamnopyranoside hydrochloride (6)

0.5 g of (5) (1.8 mmol) and 0.8 g of 1,3-diaminopropan-2-ol (9 mmol) are dissolved in 20 ml of water. The pH of the solution is adjusted to 5.5 (HCl) and 1.1 g of 1-ethyl-3-(3-dimethylaminopropyl)carbodiimide (5.4 mmol) are then added. The reaction is allowed to proceed for 24 h at room temperature, with stirring. The product (6) is isolated from the reaction medium by passage over Dowex 50×2 (Na+) (eluents: 0.33 N HCl to detach the monoamines and 2 N HCl to detach the diamines). The product (6) is finally obtained.

Synthesis of the amide formed between the compound (6) and S-acetylthioglycolic acid, (7)

The product (7) is obtained by reacting equimolecular proportions of the derivative (6) and succinimidyl S-acetylthioacetate (SATA, synthesized according to Ducan et al., Anal. Biochem. (1983) 132, 68–73) in the presence of triethylamine (1 eq.) in anhydrous dimethylformamide. The product (7) obtained is used in the following operations without particular purification.

Deprotection of the thiol group of the compound (7): synthesis of the derivative of formula (I)

A thiol group is generated on the product (7) (1 eq.), under argon, with the aid of a large excess of hydroxylamine (50 eq.) in a 0.15 M aqueous solution of EDTA, pH=7.5. The reaction is followed by spectrophotometric determination of the thiols using Ellman's reagent in accordance with the method of P. W. RIDDLES et al., Anal. Biochem. (1978) 94, 75–81. It is complete after 1 h. The resulting product of formula (I) is used quickly for grafting on to the liposomes.

B. Preparation of Liposomes Carrying Maleimide Groups

These liposomes are prepared by a conventional method, for example as in Example 1. The composition of the lipid phase is a mixture of the following compounds in molar proportions of 10:2:7:

dipalmitoylphosphatidylcholine (DPPC)

N-[4-(p-maleimidophenyl)butyryl]dipalmitoylphosphatidylethanolamine (MPB-DPPE)

cholesterol (chol)

MPB-DPPE is a phospholipid carrying a maleimide group, prepared in accordance with the method described by Martin F. J. and Papahadjopoulos D., J. Biol. Chem. (1982) 257, 286–288, by reacting dipalmitoylphosphatidylethanolamine with succinimidyl 4-p-maleimidophenyl)butyrate (SMPB).

C. Preparation of Rhamnosylated Liposomes

The method described by Martin F. J. and Papahadjopoulos D. (reference cited above) is followed.

Thus 6 μmol of the compound of formula (I) prepared in step A are added to 0.67 ml of an aqueous suspension of the liposomes prepared in step B, buffered to pH 6.5.

The mixture is placed under an argon atmosphere for 12 h at ordinary temperature, with gentle stirring.

The thiol group of the compound of formula (I) then binds to the double bond of the maleimide group by means of an addition reaction.

This gives liposomes containing, on the surface, rhamnosylated residues located at the end of a chain of atoms (spacer arm) corresponding to the chain of the compound of formula (I).

EXAMPLE 3 ACCORDING TO THE INVENTION

Preparation of Liposomes Carrying Rhamnosylated Residues Via Spacer Arms

The composition of the lipid phase is a mixture of the following compounds in molar proportions of 4:4:1:1:

Dipalmitoylphosphatidylcholine (DPPC)

Cholesterol (chol)

Dicetyl phosphate (DCP)

Asiaticoside (C.A.)

The asiaticoside is extracted from the plant Centella asiatica available for example from Inverni della Beffa, and has the formula [(O-α-L-rhamnopyranosyl-(1-4)-O-β-D-glucopyranosyl-(1-6)]-O-β-D-glucopyranose L-asiatate (MW=959 g).

The constituents of the above lipid phase are dissolved at a concentration of about 10% in a mixture of methylene chloride and methanol (80:20 by volume).

The organic solution is atomized at about 60° C. in accordance with the method described in European patent document B1-0 087 993 to give a powder.

This powder is then dispersed by stirring in the aqueous solution to be encapsulated, at a rate of 1 part of powder to 100 parts of aqueous solution. This solution can for example contain a fluorescent marker such as 5-(6)-carboxyfluorescein, as in Example 1.

A suspension of liposomes is thus formed which is preferably homogenized, for example by means of a homogenizer under pressure, as described in European patent document B1-0 107 559.

This gives a suspension of liposomes containing, on the surface, rhamnosylated residues linked to the bilayer by spacer arms consisting of the (1-4)-O-$\beta$-D-glucopyranosyl-(1-6)-O-$\beta$-D-glucopyranosyl residue.

EXAMPLE 4 ACCORDING TO THE INVENTION

Preparation of Liposomes Carrying Galactosylated Residues on the Surface

The procedure of Example 1 is followed except that digalactosyldiglyceride extracted from wheat flour, available for example from Sigma and containing two galactosylated residues at the end of the molecule, is used in place of the product according to the invention used in Example 1.

EXAMPLE 5 ACCORDING TO THE INVENTION

Preparation of Fluorescent Nanoparticles Containing Rhamnosylated Residues on the Surface Nanoparticles in the form of beads with a mean diameter of about 0.5 $\mu$m, consisting mainly of polystyrene and possessing $NH_3^+$ groups on the surface, are commercially available. Such nanoparticles are available for example from Interfacial Dynamics Corporation (I.D.C., Portland, Ore., USA).

It is therefore possible, by operating in accordance with step A of Example 1, to couple rhamnosylated residues to these nanoparticles.

This is done by reacting 0.6 g of these beads with 9 $\mu$mol of $\alpha$-L-rhamnopyranoside phenylisothiocyanate in 5 ml of bicarbonate buffer at pH 9.5 for 5 h at 4° C., with gentle stirring.

The beads are subsequently collected and then rinsed twice with PBS.

This gives nanoparticles containing rhamnosylated residues on the surface.

EXAMPLE 6 ACCORDING TO THE INVENTION

Preparation of a Neoglycoprotein Carrying Rhamnosylated Residues

A protein, for example bovine serum albumin, BSA, is used in the present case; about twenty units of rhamnose are coupled to said protein to give a neoglycoprotein.

This neoglycoprotein, called rhamnosylated BSA, is obtained by a method based on that described by MacBroom et al. in Methods in Enzymology (1972) 28, 212–222.

This method comprises dissolving 250 mg (about 1 mmol) of PPITC-$\alpha$-L-rhamnopyranoside, prepared as indicated in Example 1, in 2 ml of a 0.15 M aqueous solution of NaCl and adding 300 g of BSA. The pH is adjusted to 9.0 with NaOH (1 N). After 6 h at room temperature, with stirring, the reaction mixture is dialyzed for 16 h at 4° C. against 2 l of 0.15 M NaCl of pH 7.0. The rhamnosylated BSA is purified further by passage over a Sephadex G25 column (10 ml of gel presaturated with BSA on a column of 0.5×20 cm). The absence of any contamination by free rhamnose residues is verified by thin layer chromatography, where the rhamnosylated BSA does not migrate whereas the rhamnosylated reagent would have an Rf of 0.32 (1/1 chloroform/MeOH). Quantitative analysis of the proteins in conjunction with quantitative analysis of the sugars makes it possible to determine a grafting ratio of 10 to 30 rhamnose residues per BSA molecule, depending on the preparation in question.

EXAMPLE 7 ACCORDING TO THE INVENTION

Preparation of a Neoglycoprotein Carrying Galactose-6-phosphate Residues

In a first step, p-aminophenyl-6-phospho-$\alpha$-D-galactopyranoside is prepared from commercial p-nitrophenyl-$\alpha$-D-galactoside, in accordance with the method described by G. N. SANDO and E. M. KARSON in Biochemistry (1980) vol. 19, No. 16, pages 3850–3855, by phosphorylation with phosphoryl chloride followed by hydrogenation.

In a second step, PPITC-6-phospho-$\alpha$-D-galactopyranoside (PPITC-G) is prepared in accordance with the method of Example 1 by reacting thiophosgene with the compound prepared in the first step.

Finally, in a third step, 10 mg of bovine serum albumin (BSA) are allowed to incubate in the presence of 62 mg of PPITC-G, prepared in the previous step, by following the procedure of Example 6.

This gives BSA coupled to about twenty 6-phospho-$\alpha$-D-galactoside residues.

COMPARATIVE EXAMPLE 8

Preparation of Liposomes Carrying Glucosylated Residues on the Surface

In this Example, the procedure of Example 1 is followed except that a molecule of natural origin already carrying a glucosyl residue, which consists of the sericoside extracted from the roots of *Terminalia sericea*, available for example from Inverni Della Beffa, is used in place of the DPPE-Rha.

EXAMPLE 9

Determination of the Specificity of the Products According to the Invention Towards the Membranes of Keratinocytes The specificity of the products according to the invention, carrying oside ligands, towards the membrane of keratinocytes could be determined by using fluorescent neoglycoproteins synthesized by the inventors, the endocytosis of which can be observed by various techniques. It should be noted that the endocytosis is the greater, the more the binding at the cell membrane is specific, so that observation of the endocytosis indirectly measures the specificity of the binding of the products according to the invention. These various techniques include:

a) fluorescence microscopy, which permits qualitative cytochemical visualization of the fluorescent derivatives; and b) cytofluorimetry of the suspended cells, which makes it possible, by virtue of a cell-by-cell analysis, to specify the distribution of the fluorescent molecules within the cell population as a whole. Moreover, this technique opens up the possibility of a simultaneous analysis of various parameters (size, cell shape, double labeling with monoclonal antibodies or study of the cell cycle with the aid of markers specific for DNA or RNA).

Each of these methods is described in detail below following an explanation of the cell cultures used.

The cells used are normal human fibroblasts (F26) and tumoral human keratinocytes (HSC).

The culture media are obtained from EUROBIO and are as follows:

for the fibroblasts:

Eagle's minimum essential medium (MEM), which is well known to those skilled in the art, for the keratinocytes:

a Ham F12 medium to which a Dulbecco modified Eagle's minimum essential medium (DMEM) has been added, said media also being well known to those skilled in the art.

These media are complemented with fetal calf serum (10%), penicillin-streptomycin (100,000 IU/l and 0.1 g/l) and mycostatin (100,000 IU/l).

The culture conditions are as follows:

For the study by fluorescence microscopy

The keratinocytes are cultivated on glass slides, which serve as the support.

This is done by placing a slide at the bottom of each well in a 24-well culture plate of the Linbro type (diameter 14 mm).

Culture:
20,000 cells/well
volume 200 $\mu$l/well
incubation:
temperature 32° C.
humidity 96%
$CO_2$ level 5%
culture time: 5 days to attain cell confluence For the study by flux cytometry The culture is prepared in Petri dishes of diameter 60 mm (CORNING).

Culture:
200,000 cells/dish
volume 2 ml/dish
incubation:
temperature 37° C.
humidity 96%
$CO_2$ level 5%
culture time: 7 to 12 days to attain cell confluence A. Fluorescence Microscopy The cells can be studied in situ by fluorescence microscopy. It is possible to locate those parts of the cell where the fluorescent compounds bind preferentially.

The substances tested are neoglycoproteins synthesized from BSA by reaction with a glycosido-p-phenylisothiocyanate in accordance with Example 6 or, where appropriate, Example 7 if it is desired to obtain a phosphated sugar. These neoglycoproteins are then rendered fluorescent by reaction with fluorescein p-phenylisothiocyanate.

These molecules will be detected by fluorescence analysis of the fluorescein in the knowledge that the latter has a maximum excitation wavelength $\lambda_{ex}=490$ nm and a maximum emission wavelength at 517 nm.

A Zeiss® microscope equipped for "epifluorescence" is used in the present case. Excitation is produced by light whose wavelength is selected by a filter. Likewise, a second filter only transmits the emitted light at wavelengths of between 520 and 560 nm.

The cells, cultivated on slides, are labeled with a neoglycoprotein in the following manner. The medium in the keratinocyte culture dishes is replaced with a solution of neoglycoprotein in PBS at a concentration of 1 mg/ml. Incubation is allowed to proceed for 2 h at 32° C. The product is then rinsed in culture with PBS at 4° C. and fixed with paraformaldehyde. A similar procedure is followed with fluorescent BSA as a standard substance.

With a second batch of dishes, incubation is carried out for 1½ h at 32° C., monensin is then added to the medium at a rate of 1 $\mu$g/ml and incubation is continued for 30 min at 4° C., the purpose of this operation being to raise the intracellular pH so as to increase the sensitivity of the fluorimetric measurement.

With a third batch of dishes, after incubation at 32° C. for 2 h and fixing with paraformaldehyde, the plastic membrane is rendered permeable with a detergent such as Nonidet P40®, available from SIGMA. Rendering the membrane permeable in this way makes it possible to facilitate access of the internal membranes to the fluorescent products, enabling sugar receptors to be detected inside the cell.

Observation makes it possible to locate the fluorescence emitted in the different parts of the cell:

$V_{mb}$: vesicles at the membranes
$V_c$: vesicles in the cytoplasm
$M_b$: external membrane
R: network in the cytoplasm
N: nucleus
PN: points around the nucleus The results of these observations are collated in Table 1 below for neoglycoproteins which differ from one another by the nature of the oside residues they carry.

It is very clearly apparent that the fluorescence is intense, or even very intense, at the cell membrane in the case of rhamnose, galactose-6-phosphate and, to a considerably lesser extent, galactose.

This study clearly shows the existence of a specific affinity of keratinocyte membrane receptors for rhamnose, galactose and galactose-6-phosphate residues and more particularly for $\alpha$-L-rhamnose and $\alpha$-D-galactose-6-phosphate.

TABLE 1

| Fluorescence intensity of keratinocytes labeled with fluorescent neoglycoproteins | | | |
|---|---|---|---|
| Fluorescent neoglycoprotein | 32° C. (2 h) | 32° C. (2 h) + monensin | Cells rendered permeable (2 h) with Nonidet P40® |
| FBSA (standard) | — | — | — |
| FBSA Glc $\alpha$ | $V_c+$ | $V_c++$ | $N++$ $PN++$ $R+$ |
| FBSA Glc Nac $\beta$ | $V_c+$ | $V_c++$ | $N++$ $PN++$ $R+$ |
| FBSA Gal $\alpha$ | $V_c\pm$ $V_{mb}+$ $M_b+$ | $V_c+$ $V_{mb}+$ $M_b+$ | $N++$ $PN++$ $R\pm M_b+$ |
| FBSA Fuc $\alpha$ | — | — | — |
| FBSA Lac $\beta$ | $V_c\pm$ | $V_c\pm$ | $N\pm$ $PN+$ |
| FBSA Man $\alpha$ | — | — | $PN+$ |
| FBSA Man 6P $\alpha$ | $V_c\pm$ | $V_c+$ | $N\pm$ $PN+++$ |
| FBSA Rha $\alpha$ | $V_c++$ $V_{mb}+++$ $M_b+$ | $V_c+++$ $V_{mb}+++$ $M_b+$ | $N+++$ $PN++$ $M_bR++$ |

TABLE 1-continued
Fluorescence intensity of keratinocytes labeled with fluorescent neoglycoproteins

| Fluorescent neoglycoprotein | 32° C. (2 h) | 32° C. (2 h) + monensin | Cells rendered permeable (2 h) with Nonidet P40 ® |
|---|---|---|---|
| FBSA Gal 6P α | $V_c^{++} V_{mb}^{+++} M_b^{\pm}$ | $V_c^{+++} V_{mb}^{++++} M_b^{\pm}$ | $N^{+++} PN^{++} M_bR^{++}$ |

Fluorescence intensity:
$\pm$ very weak
$^+$weak
$^{++}$moderate
$^{+++}$strong
$^{++++}$very strong
Glc: α-D-glucose
Glc Nac: N-acetyl-D-glucosamine
Gal: α-D-galactose
FBSA: fluorescent bovine serum albumin
Fuc: α-L-fucose
Lac: β-lactose
Man: α-D-mannose
Man 6P: α-D-mannose-6-phosphate
Rha: α-L-rhamnose
Gal 6P: α-D-galactose-6-phosphate

B. Technique Using Flux Cytofluorimetry (FCM)

1. Principle

When the cells, cultivated in Petri dishes of diameter 60 mm, have attained confluence, they are brought into contact with the products according to the invention which contain at least one oside ligand. For example, in a particularly advantageous embodiment of the invention, these products according to the invention which carry oside ligands are incorporated into the lipid phase of liposomes and end up on the surface of the liposomes with the oside ligands freely accessible from the outside.

To perform this study, it is necessary to encapsulate a fluorescent substance in the liposomes. It is preferable to use the potassium salt of 5-(6)-carboxyfluorescein [5-(6)-CF].

In this technique, the endocytosis of the different types of liposomes is compared by measurement of the 5-(6)-CF incorporated in each cell.

It is necessary to avoid using an excessive concentration of 5-(6)-CF in this technique since this could induce extinction of the fluorescence.

2. Composition of the liposomes prepared as described in Example 1

| "Bare" liposome (without sugar) T | |
|---|---|
| Composition | DPPC/DCP/chol 5/1/4 in mol |
| Concentrations | 100 mg/10 ml → 1% |
| Liposome PE-Rha (rhamnose model) (= Example 1 of the invention) | |
| Composition | PE-Rha/DPPC/DCP/chol 1/4/1/4 in mol |
| Concentrations | 100 mg/10 ml → 1% |
| Liposome asiaticoside (glucose-glucose-rhamnose) (= Example 3 of the invention) | |
| Composition | C.A./DPPC/DCP/chol 1/4/1/4 in mol |
| Concentrations | 100 mg/10 ml → 1% |
| Liposome sericoside (glucose) (= Comparative Example 8) | |
| Composition | SER/DPPC/DCP/chol 1/4/1/4 in mol |
| Concentrations | 100 mg/10 ml → 1% |
| The encapsulated fluorescent compound | |
| 5-(6)-CF | 50 mM in PBS |

3. Method

Each liposome suspension, purified on a column, is diluted 2-fold in culture medium.

2 ml of liposome suspension are distributed into each dish (60 mm).

The blank is prepared with culture medium.

The Petri dishes are placed in an oven (37° C.) for 1 h 30 min.

The dishes are rinsed twice with 5 ml of PBS.

The cells are detached from the plastic support:
for the fibroblasts: 0.25% trypsin
for the keratinocytes: 0.25% trypsin+0.02% EDTA The cells are recovered and centrifuged at 1500 rpm (JOUAN E 96 centrifuge) at 4° C.

The supernatant is discarded and the cell residue is resuspended in 50 μl of propidium iodide (P.I.) at a final concentration of 50 μg/ml in PBS (viability test).

The suspension is filtered on bolting cloth (pore diameter: 60 μm) to remove the aggregates.

The cells are then kept in ice until analyzed.

4. Measurements

The measurements are made with a flux cytofluorimeter (EPICS Profile Coultronics) using an excitation wavelength $\lambda_{ex}$ of 488 nm. The emission wavelengths ($\lambda_{em}$) are as follows:

$\lambda_{em}$ (5-(6)-CF)=520 nm (green)

$\lambda_{em}$ (P.I.)=620 nm (red)

A first two-parameter histogram, cell size=f(cell density), makes it possible to determine the cell population (A).

This population will be analyzed by red fluorescence (B). Only the non-fluorescent (living) cells will be considered for analysis by green fluorescence (C).

Analysis of the cells by green fluorescence will make it possible to assess the incorporation of the different liposomes labeled with 5-(6)-CF (C). (cf. FIG. 1).

(cf. FIG. 1: THE DIFFERENT HISTOGRAMS permitting analysis of the cell population by FCM according to the proposed protocol A: granulosity=f(size)→isolation of the population to be analyzed (window 1)

B: number of cells=f(red fluorescence)→viability test. The analysis will only be performed for the living cells (window 2).

C: number of cells=f(green fluorescence)→analysis of the 5-(6)-CF incorporated in the cells)

The intrinsic fluorescence of the cells (blank) will be subtracted from each sample.

The following Table 2 is obtained:

TABLE 2

Figure 1A:
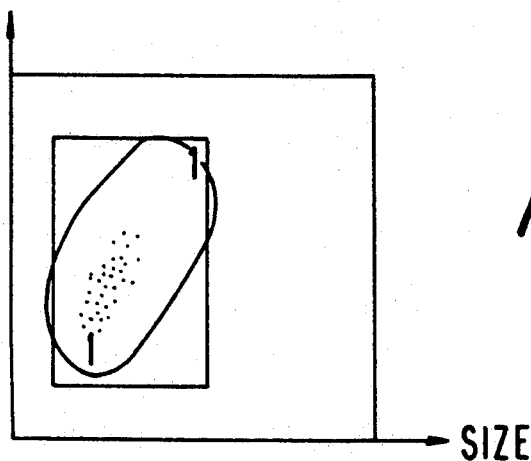
FIG. 1A shows granulosity=f(size)→isolation of the population to be analyzed.
Figure 1B:
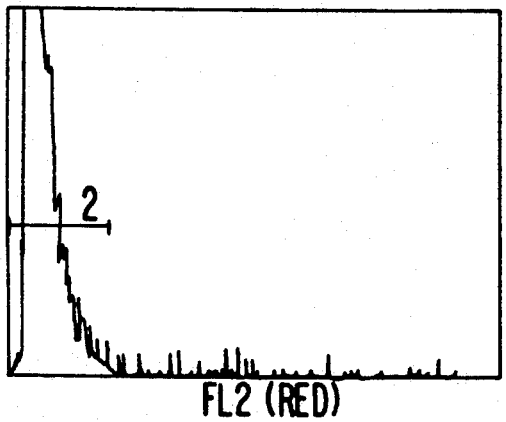
FIG. 1B shows number of cells=f(red fluorescence)→viability test.
Figure 1C:
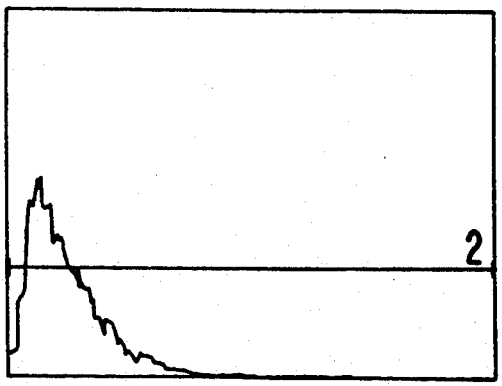
FIG. 1C shows number of cells=f(green fluorescence)→analysis of the 5-(6)-CF incorporated in the cells.
Figure 2A:
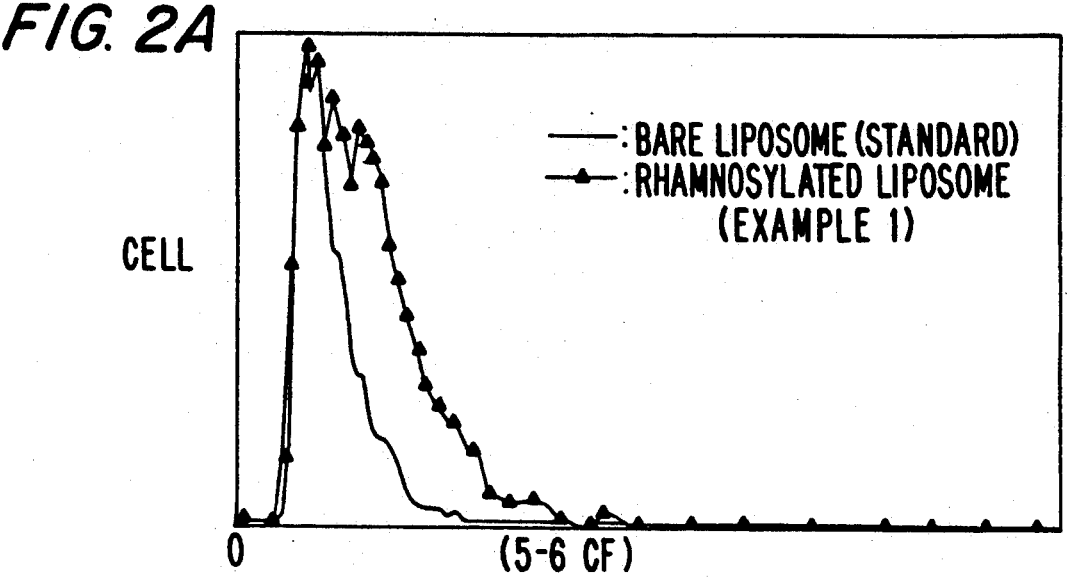
FIG. 2 shows the single-parameter histograms obtained by this flux cytometry (FCM) technique, showing the incorporation of the contents of the liposomes into the keratinocytes (number of cells=f(incorporated 5-(6)-CF); cell type: keratinocytes; number analyzed: 7000 cells, after interaction with different liposomes encapsulating 5-(6)-CF; incubation: 1 h 30 min).
Figure 2B:
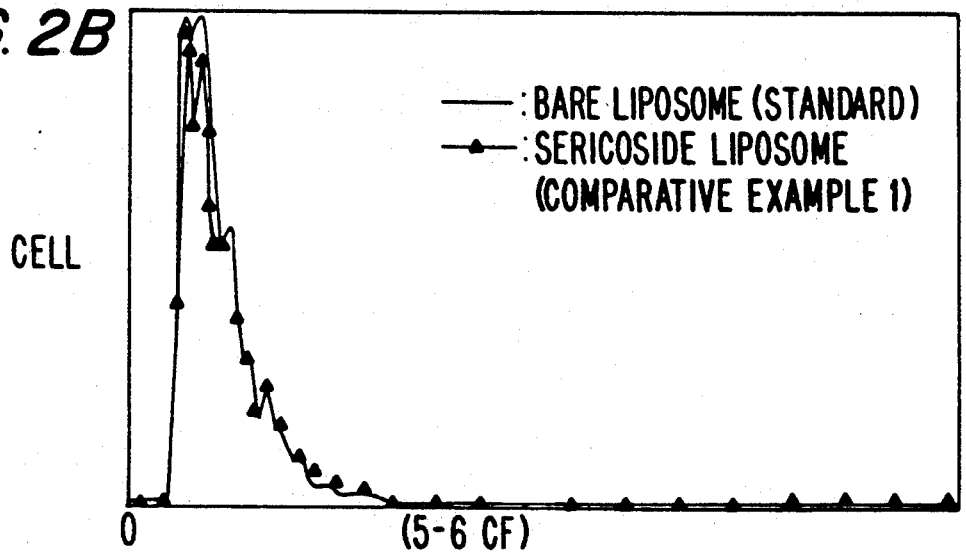
Figure 2C:
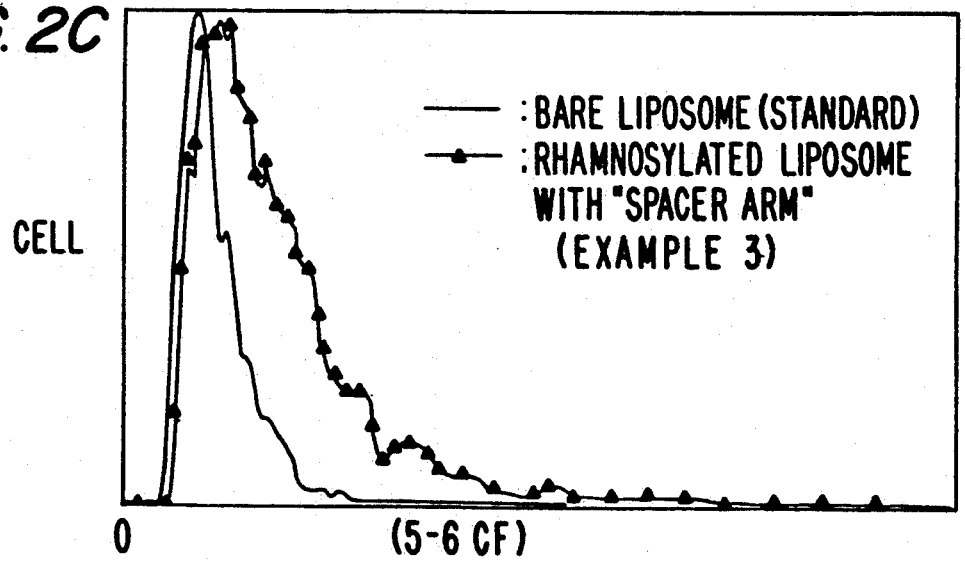

| Liposomes | relating to FIG. 2 | |
|---|---|---|
| | Average fluorescence (A.U.) | Ratio to the standard Test/standard |
| Standard | 28.3 | 1 |
| SER | 28.9 | 1.0 |
| PE-Rha | 39.1 | 1.4 |
| C.A. | 47.1 | 1.7 |

A.U.: arbitrary unit

It is seen from Table 2 and FIG. 2 that the liposomes carrying rhamnose, referred to as PE-Rha, undergo endocytosis more rapidly than the liposomes possessing glucose of the sericoside molecule, referred to as SER. Furthermore, the endocytosis of the liposomes containing the asiaticoside, referred to as C.A., is more substantial than that of PE-Rha.

It is observed that the structures of the asiaticoside and DPPE-Rha molecules are very different and that the only point common to both is the presence of rhamnose at the end of the chain.

This demonstrates that it is this sugar (ligand) which is responsible for the increase in the incorporation of the liposomes into the keratinocytes by endocytosis. It will also be observed that the liposome containing the asiaticoside on its surface (C.A.) undergoes endocytosis more rapidly, doubtless due to the presence of the glucosylglucose spacer arm, which makes it more accessible to its keratinocyte membrane receptor than PE-Rha.

Turning to the incorporation of these liposomes into fibroblasts, the fibroblasts are cultivated as described above. This gives the single-parameter histograms of FIG. 3 (number of cells=f(incorporated 5-(6)-CF); cell type: fibroblasts; number analyzed: 5000 cells, after interaction with different liposomes encapsulating 5-(6)-CF; incubation: 1 h 30 min) and the following Table 3:

TABLE 3

Figure 3A:
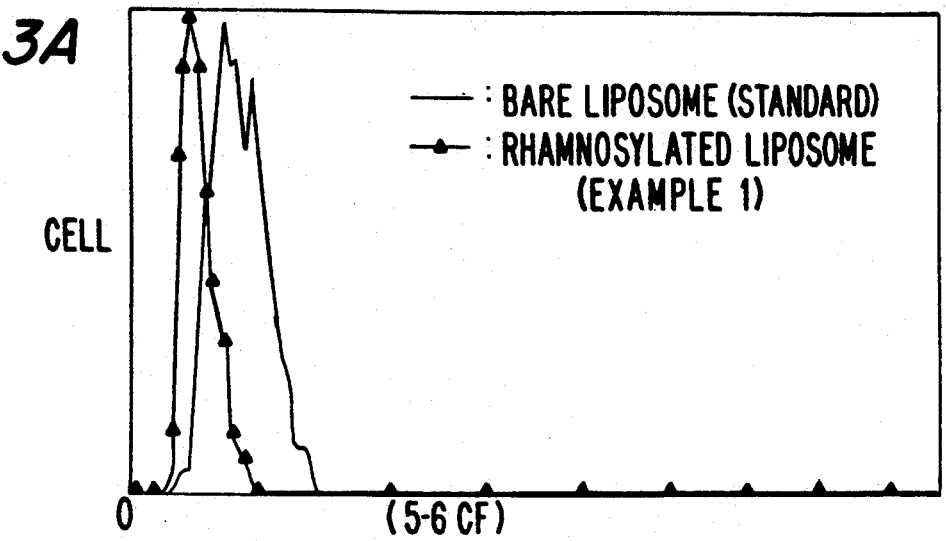
FIG. 3 shows incorporation of lipsomes into fibroblasts.
Figure 3B:
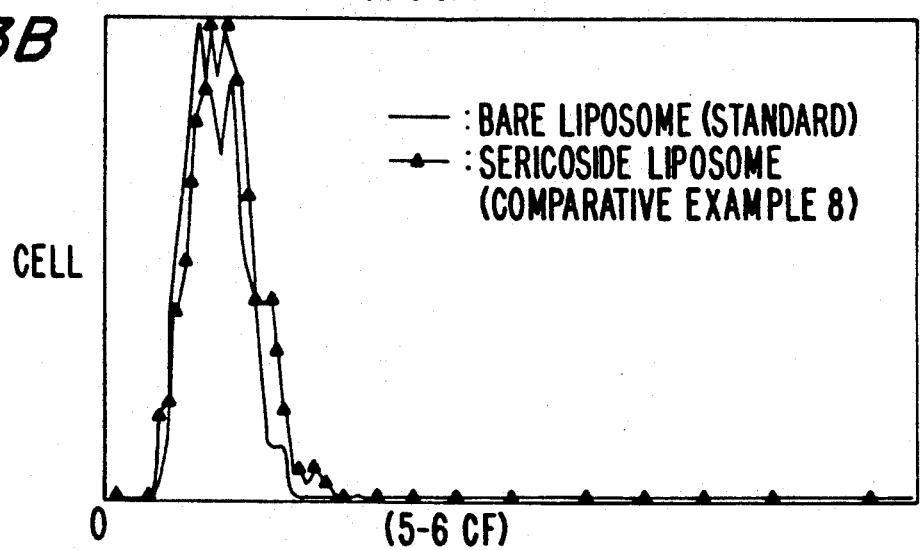
Figure 3C:
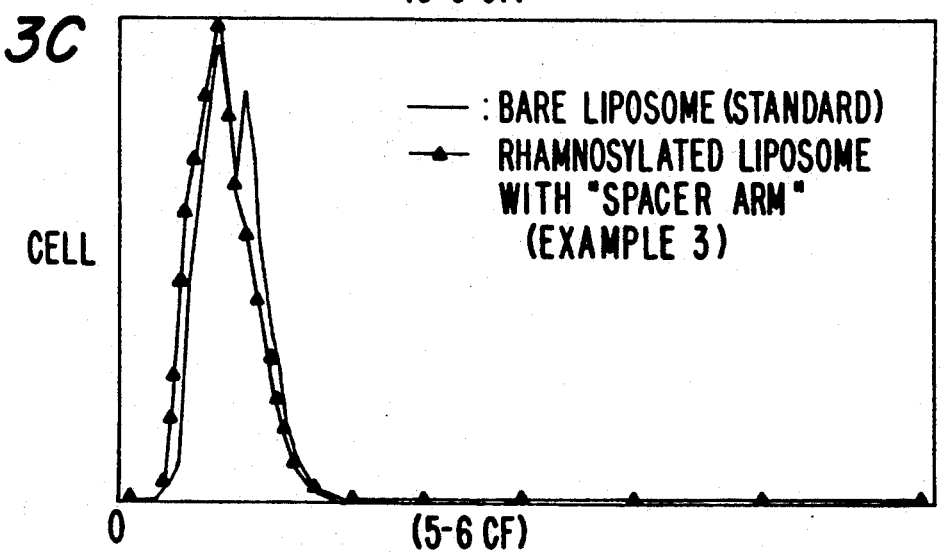

| Liposomes | relating to FIG. 3 - Fibroblasts | |
|---|---|---|
| | Average fluorescence (A.U.) | Ratio to the standard Test/standard |
| Standard | 34.4 | 1 |
| SER | 37.0 | 1.1 |
| PE-Rha | 22.0 | 0.6 |
| C.A. | 32.6 | 0.9 |

A.U.: arbitrary unit

It can be seen that, as regards fibroblasts, no liposome seems to undergo endocytosis more readily than the standard liposome.

It can be concluded from the above fluorescence analyses that the liposomes which have in their membrane composition molecules containing a rhamnose, galactose or galactose-6-phosphate ligand are better incorporated into keratinocytes by endocytosis. In addition, it is observed that α-L-rhamnose and α-D-galactose-6-phosphate have an appreciably greater specificity for the keratinocyte membrane receptors than α-D-galactose.

On the other hand, fibroblasts are indifferent to these molecules and to the structure of the glucose carried by the sericoside. It must therefore be concluded from this that products according to the invention which contain at least one oside residue consisting of rhamnose, galactose or galactose-6-phosphate, and more particularly α-L-rhamnose and α-D-galactose-6-phosphate, can be bound specifically to the surface of the membranes of keratinocytes.

Various Examples of cosmetic or pharmaceutical compositions, especially dermatological compositions, incorporating products according to the invention will now be given.

EXAMPLE 10

Cosmetic Anti-Wrinkle Cream

The cream is obtained by mixing an emulsion and a gelled suspension of liposomes having the following compositions:

| | |
|---|---|
| emulsion: | |
| perhydrosqualene | 39.2 g |
| soya lecithin | 0.8 g |
| distilled water ad | 220.0 g |
| gelled suspension of liposomes: | |
| dipalmitoylphosphatidylcholine (DPPC) | 0.49 g |
| cholesterol (chol) | 0.26 g |
| dicetyl phosphate (DCP) | 0.09 g |
| rhamnosylated DPPE (Example 1) | 0.16 g |
| elastin polypeptides | 0.5 g |
| calf thymus hydrolyzate | 0.1 g |
| Carbopol 940 ® | 1.0 g |
| triethanolamine | 1.0 g |
| distilled water, perfumes and preservatives ad | 100.0 g |

A mixture of perhydrosqualene (39.2 g) and soya lecithin (0.8 g) is heated in a water bath at 70° C. for 15 min. The oily phase obtained is taken up with 180 ml of distilled water and then emulsified by means of a Raynerie agitator.

In a separate operation, a gelled suspension of liposomes is prepared in the following manner. The liposomes are prepared as indicated in Example 1. The constituents of the lipid phase (DPPC, chol, DCP, DPPE-rhamnose) are dissolved in a 7:1 chloroform/methanol mixture. The resulting organic solution is evaporated under reduced pressure and the lipid residue is then taken up with 49 g of an aqueous solution containing the substances to be encapsulated (elastin polypeptides and calf thymus hydrolyzate prepared for example by the method described in French patent document A1-2 594 847). After sonication, a homogenized suspension of liposomes is thus obtained. Finally, this suspension is gelled by the addition of 50 g of 2% Carbopol 940 ® gel neutralized with triethanolamine, which has been prepared in conventional manner.

This cream is applied daily to the skin of the face and neck.

EXAMPLE 11

Lotion for Treating Psoriasis

| Composition: | |
|---|---|
| Dipalmitoylphosphatidylcholine (DPPC) | 2.2 g |
| cholesterol (chol) | 1.16 g |
| dicetyl phosphate (DCP) | 0.41 g |
| asiaticoside (C.A.) | 0.73 g |
| theophylline | 1.00 g |
| preservative | 0.10 g |
| aqueous excipient gelled with Carbopol 940 ® (at 0.1%) | 100.00 g |

A lipid powder is prepared according to Example 3 by atomizing a solution in an 8:2 methylene chloride/methanol mixture containing the lipid or hydrophobic constituents (DPPC, chol, DCP, C.A.) and 0.5 g of theophylline.

This powder is then dispersed, by agitation, in 50 ml of an aqueous solution containing 0.5 g of theophylline and the dispersion is then homogenized with ultrasound by the method known to those skilled in the art.

This gives a suspension of liposomes encapsulating theophylline and containing rhamnosyl residues on the surface. Finally, this suspension is mixed with about 45 g of stabilized carbomer gel prepared in conventional manner.

The resulting lotion can be applied locally for the treatment of psoriasis, twice a day, until the lesions disappear.

EXAMPLE 12

Hair lotion

| Composition: | |
|---|---|
| soya phospholipids (SP) | 2.5 g |
| cholesterol (chol) | 1.2 g |
| dicetyl phosphate (DCP) | 0.5 g |
| asiaticoside (C.A.) | 0.8 g |
| placental extract | 5.0 g |
| sodium pantothenate | 0.1 g |
| preservative | 0.1 g |
| aqueous excipient gelled with Carbopol 940 ® (at 0.1%) ad | 100.0 g |

The procedure of Example 11 is followed except that the lipid powder does not contain theophylline.

This powder is dispersed in 50 ml of an aqueous solution containing 5 g of placental extract and 0.1 g of sodium pantothenate and the dispersion is then gelled with a sufficient amount of stabilized carbomer gel to give a final weight of 100 g of lotion.

When applied daily to the scalp, this lotion improves the state of health of the hair roots and stimulates hair growth.

What is claimed is:

1. A method of binding a product to the membrane of a keratinocyte by means of a ligand-receptor bond, which comprises using a product comprising at least one ligand consisting of an oside residue accessible to the membrane receptors, said oside residue being selected from rhamnose, galactose and galactose-6-phosphate.

2. The method defined in claim 1 wherein said oside residue is alpha-L-rhamnose.

3. The method defined in claim 1 wherein said oside residue is alpha-D-galactose-6-phosphate.

4. The method according to claim 1 wherein the ligand is coupled to the surface of said product by a covalent chemical bond.

5. The method according to claim 1 wherein said ligand is coupled to the surface of said product via a spacer arm.

6. The method according to claim 5 wherein said spacer arm is the residue of a heterobifunctional reagent.

7. The method defined in claim 5 wherein the spacer arm is a combination of several sugars.

8. The method according to claim 7 wherein said group of several sugars is the (1-4)-O-β-D-glucopyranosyl-(1-6)-O-β-β-D-glucopyranosyl group.

9. The method according to claim 5 wherein said product is a submicroscopic particle comprising a liposome or a polymeric nanoparticle.

10. The method according to claim 1 wherein said product is a molecule or macromolecule of natural or synthetic origin.

11. The method according to claim 10 wherein said molecule or macromolecule is an asiaticoside, a digalactosyldiglyceride or a neoglycoprotein.

12. The method according to claim 11, wherein said neoglycoprotein is obtained by combining a serum albumin with a sugar selected from the group consisting of rhamnose, galactose and galactose-6-phosphate.

13. The method according to claim 1 wherein the product is or contains a substance of cosmetic pharmaceutical or dermatological interest.

14. The method of claim 13 wherein said substance comprises an agent for modulating the metabolism of skin cells.

15. The method according to claim 1 of selecting a product which is to be bound to the membrane of a keratinocyte by means of a ligand-receptor bond, which comprises isolating from a group of products comprising at least one ligand consisting of an oside residue accessible to the membrane receptors, said oside residue being selected from rhamnose, galactose and galactose-6-phosphate.

16. The method of claim 15 wherein said oside residue is α-L-rhamnose.

17. The method of claim 15 wherein said oside residue is α-D-galactose-6-phosphate.

18. The method of claim 15 wherein said product is a molecule or macro-molecule of an asiaticoside.

19. A method of preparing a product which is to be bound to the membrane of a keratinocyte by means of a ligand-receptor bond, which comprises coupling to said product at least one ligand consisting of an oside residue accessible to the membrane receptors, said oside residue being selected from rhamnose, galactose or galactose-6-phosphate.

20. The method according to claim 19 wherein said oside residue is α-L-rhamnose.

21. The method according to claim 19 wherein said oside residue is α-D-galactose-6-phosphate.

22. The method according to claim 19 wherein said ligand is coupled to the surface of said basic structure by a covalent chemical bond.

23. The method according to claim 19 wherein said ligand is coupled to the surface of said product via a spacer arm.

24. The method according to claim 23 wherein said spacer arm is the residue of a heterobifunctional reagent.

25. The method according to claim 23 wherein said spacer arm is a group comprising several sugars.

26. The method according to claim 25 wherein said group of several sugars is (1-4)-O-β-D-glucopyranosyl-(1-6)-O-β-D-glucopyranosyl group.

27. The method according to claim 19 wherein said product is a submicroscopic particle comprising a liposome or a polymeric nanoparticle.

28. The method according to claim 27 wherein the proportion of oside residues, as a molar percentage of all the lipid molecules forming the bilayer of the liposome, is at least 10% relative to all the amphiphilic lipids.

29. The method according to claim 28 wherein the proportion of oside residues, as a molar percentage of all the lipid molecules forming the bilayer of the liposome, is at least 15% relative to all the amphiphilic lipids.

30. The method according to claim 28 wherein said liposomes are formulated so as to have a high microviscosity.

31. The method according to claim 19 wherein said product used is a molecule or macromolecule of natural or synthetic origin.

32. The method according to claim 31 wherein said product is a protein.

33. The method according to claim 32 wherein said protein is a serum albumin.

34. The method according to claim 19 wherein said product contains a substance of cosmetic, pharmaceutical or dermatological interest, comprising an agent for modulating the metabolism of the skin cells.

35. The method according to claim 34 wherein said product is a substance of cosmetic, pharmaceutical or dermatological interest, comprising an agent for modulating the metabolism of skin cells.

36. A product which is the chemical reaction product of at least one ligand consisting of an oside residue, said oside residue being selected from rhamnose, galactose and galactose-6 phosphate, and a compound consisting of a submicroscopic particle, a natural molecule, a natural macromolecule, a molecule of synthetic origin, a, a substance having cosmetic applications, a substance having pharmaceutical applications and a substance having dermatological applications.

37. The product according to claim 36 wherein said submicroscopic particle is a liposome.

38. The product according to claim 37 wherein said liposome carries α-L-rhamnosyl or α-D-galactosyl-6-phosphate residues on the surface.

39. The product according to claim 36 wherein said submicroscopic particle is a polymeric nanoparticle.

40. The product according to claim 39 wherein said polymeric nanoparticle carries a residue on the surface selected from the group consisting of α-D-galactosyl, α-L-rhamnosyl or α-D-galactopyranosyl-6-phosphate.

41. The product according to claim 36 wherein said macromolecule of natural original is a protein.

42. The product according to claim 41 wherein said protein is serum albumin.

43. A product according to claim 41 wherein the number of said oside residues carried by a protein is at least about 20.

44. The product defined in claim 36 wherein said chemical reaction comprises coupling said ligand to the surface of said compound by means of a covalent chemical bond.

45. The product according to claim 44 wherein said coupling is effected via a spacer arm.

46. The product according to claim 45 wherein said spacer arm is a residue of a heterobifunctional reagent.

47. The product according to claim 45 wherein said spacer arm is a group of several sugars.

48. The product according to claim 47 wherein said group of sugars is the (1-4)-O-β-D-glucopyranosyl-(1-6)-O-β-D-glucopyranosyl group.

49. The product defined in claim 44 wherein said substance is an agent for modulating the metabolism of skin cells.

50. The product according to claim 36 which is selected from the group consisting of an asiaticoside extracted from the plant *Centella asiatica*, a digalactosyldiglyceride and a neoglycoprotein obtained by combining serum albumin with α-L-rhamnosyl or α-D-galactose-6-phosphate.

51. A composition, suitable for cosmetic, pharmaceutical or dermatological uses, which contains at least one product as defined by claim 36.

52. The composition according to claim 51 which is intended for treatment affecting keratinocytes, suitable for the improvement of skin regeneration, the treatment of psoriasis or renewed hair growth.

53. A method of preparing a composition having, cosmetic, pharmaceutical or dermatological uses, wherein at least one product as defined in claim 36, is associated with a cosmetically or pharmaceutically acceptable excipient, vehicle or carrier.

54. A method of skin care using a treatment affecting the keratinocytes, comprising applying a product consisting of at least one ligand consisting of an oside residue accessible to membrane receptors, said oside residue being selected from rhamnose, galactose and galactose-6-phosphate, alpha-L-rhamnose and alpha-D-galactose-6-phosphate, in a cosmetically or therapeutically effective amount.

55. The method of claim 54, wherein the oside residue is selected from alpha-L-rhamnose and alpha-D-galactose-6-phosphate.

56. The method defined in claim 54 wherein said product is in contact with a cosmetically or pharmaceutically acceptable vehicle, carrier or excipient.

57. The method of skin care defined in claim 54 which is suitable for skin regeneration.

58. The method of skin care defined in claim 54 which is suitable for the treatment of psoriasis.

59. The method of skin care defined in claim 54 which is suitable for stimulating hair growth.

* * * * *